(12) United States Patent
Penning et al.

(10) Patent No.: US 8,148,384 B2
(45) Date of Patent: Apr. 3, 2012

(54) SUBSTITUTED THIENO[3,2-D]PYRIMIDINE PIM KINASE INHIBITORS AS CANCER CHEMOTHERAPEUTICS

(75) Inventors: Thomas D. Penning, Elmhurst, IL (US); Lisa A. Hasvold, Grayslake, IL (US); Laura A. Hexamer, Grayslake, IL (US); Vincent L. Giranda, Gurnee, IL (US); Nan-horng Lin, Vernon Hills, IL (US); Zhi-Fu Tao, Gurnee, IL (US); Le Wang, Vernon Hills, IL (US)

(73) Assignee: Abbott Laboratories, Abbott Park, IL (US)

( * ) Notice: Subject to any disclaimer, the term of this patent is extended or adjusted under 35 U.S.C. 154(b) by 755 days.

(21) Appl. No.: 11/951,546

(22) Filed: Dec. 6, 2007

(65) Prior Publication Data

US 2008/0161559 A1 Jul. 3, 2008

Related U.S. Application Data

(60) Provisional application No. 60/882,618, filed on Dec. 29, 2006.

(51) Int. Cl.
*C07D 495/04* (2006.01)
*A61K 31/519* (2006.01)
*A61P 35/00* (2006.01)
*C07D 495/14* (2006.01)

(52) U.S. Cl. ............ 514/260.1; 514/267; 544/278; 544/250

(58) Field of Classification Search .......... 544/278, 544/250; 514/260.1, 267
See application file for complete search history.

(56) References Cited

U.S. PATENT DOCUMENTS

| 3,755,583 | A | 8/1973 | De Angelis et al. |
| 6,187,777 | B1 * | 2/2001 | Norman et al. ............ 514/265.1 |
| 6,469,166 | B2 * | 10/2002 | Webb et al. ............... 544/278 |
| 6,492,383 | B1 * | 12/2002 | Munchhof et al. ........... 514/301 |

FOREIGN PATENT DOCUMENTS

| EP | 0071227 B1 | 2/1983 |
| EP | 1619197 A1 | 1/2006 |
| WO | 9823620 A1 | 6/1998 |
| WO | 9849899 A1 | 11/1998 |
| WO | 2006010568 A2 | 2/2006 |

OTHER PUBLICATIONS

Athmani, et al., Azoles Part 10. "Thiazolo[4,5;4,5]thieno[3,2-d]pyrimidine, a New Heterocyclic Rung System" Tetrahedron, vol. 48 No. 36, pp. 7689-7702 (1992) XP002504194.
Database [Online] Chemical Abstracts Service, Columbus, OH; (2000-04-280, "Synthesis of novel heterocyclic compounds for anti-tumor and radioprotective activities" XP002504195. Database accession No. 2000:276401.
Dumaitre, et al., "Synthesis and Cyclic GMP Phosphodiesterase Inhibitory Activity of A Series of 6-Phenylpyrazolo [3,4-d]pyrimidones" Journal of Medicinal Chemistry, vol. 39 No. 8, pp. 1635-1644 (1996) XP000651134.
Gopal, et al., "Biological properties of 8-methoxypyrimido [4,5:4,5]thieno(2,3-b)quinoline-4(3H)-one, a new class of DNA intercalating drugs" Indian Journal of Medical Research, vol. 119 No. 5, pp. 198-205 (2004) XP008098602.
Morwick, et al., "Evolution of the Thienopyridine Class of Inhibitors of IkB Kinase-B: Part I: Hit to Lead Strategies" Journal of Medicinal Chemistry, vol. 49 No. 10, pp. 2898-2908 (2006) XP002504193.
Shishoo, et al., "Synthesis and Quantitative Structure-Activity Relationships of Antihyperlipaemic 2-substituted Thieno[3,2-d]pyrimidin-4(3H)-ones" Arzneimittel-Forschung, vol. 46 No. 3, pp. 273-276 (1996) XP008098628.
PCT, International Search Report PCT/US2007/086472, Date of mailing Nov. 27, 2008.

* cited by examiner

*Primary Examiner* — Susanna Moore
(74) *Attorney, Agent, or Firm* — Susan L. Steele

(57) ABSTRACT

Compounds of formula I

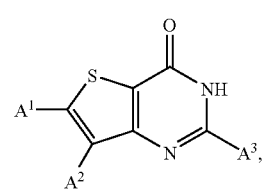

wherein $A^1$, $A^2$, and $A^3$ are as defined herein are inhibitors of PIM kinase. The compounds of formula I are useful for the treatment of diseases such as cancer.

8 Claims, No Drawings

SUBSTITUTED THIENO[3,2-D]PYRIMIDINE PIM KINASE INHIBITORS AS CANCER CHEMOTHERAPEUTICS

This application claims priority to U.S. Provisional Application Ser. No. 60/882,618 filed Dec. 29, 2006.

FIELD OF THE INVENTION

This invention relates to inhibitors of Pim kinases, ways to make them and methods of treating patients using them.

BACKGROUND OF THE INVENTION

Pim kinases are essential for facilitating DNA repair, controlling RNA transcription, mediating cell death and regulating immune response. This activity makes Pim kinase inhibitors targets for a number of disorders. Pim kinase inhibitors have shown utility for treating diseases such as ischemia reperfusion injury, inflammatory disease, retroviral infections, ischemia reperfusion injury, myocardial infarction, stroke and other neural trauma, organ transplantation, reperfusion of the eye, kidney, gut and skeletal muscle, arthritis, gout, inflammatory bowel disease, CNS inflammation such as MS and allergic encephalitis, sepsis, septic shock, hemmorhagic shock, pulmonary fibrosis, and uveitis, diabetes and Parkinsons disease, liver toxicity following acetaminophen overdose, cardiac and kidney toxicities from doxorubicin and platinum-based antineoplastic agents and skin damage secondary to sulfur mustards. Pim kinase inhibitors have also been shown to potentiate radiation and chemotherapy by increasing cell death of cancer cells, limiting tumor growth, decreasing metastasis, and prolonging the survival of tumor-bearing animals. There is therefore a need in the therapeutic arts for Pim kinase inhibitors.

SUMMARY OF THE INVENTION

One embodiment of this invention, therefore, pertains to compounds that inhibit the activity of Pim kinases and have formula I

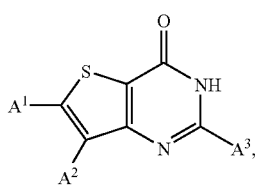

and salts thereof, wherein $A^1$ and $A^2$ are independently selected H, $R^1$, $R^2$, $R^3$, $R^4$, OH, $OR^5$, $NH_2$, $NHR^7$, $N(R^7)_2$, F, Cl, Br or I;

$R^1$ is phenyl which is unfused or fused with benzene, heteroarene, cycloalkane, cycloalkene, heterocycloalkane or heterocycloalkene;

$R^2$ is heteroarene which is unfused or fused with benzene, heteroarene, cycloalkane, cycloalkene, heterocycloalkane or heterocycloalkene;

$R^3$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^4$ is alkyl, alkenyl or alkynyl, each of which is unsubstituted or substituted with one or two of independently selected heterocycloalkyl, $CF_3$, F, Cl, Br or I;

$R^5$ is alkyl which is unsubstituted or substituted with one or two of independently selected $R^6$, OH, $OR^7$, $NH_2$, $NHR^7$ or $N(R_7)_2$;

$R^6$ is phenyl which is unfused or fused with benzene, heteroarene, cycloalkane, cycloalkene, heterocycloalkane or heterocycloalkene;

$R^7$ is H, $R^8$, $R^9$, $R^{10}$ or $R^{11}$;

$R^8$ is phenyl which is unfused or fused with benzene, heteroarene, cycloalkane, cycloalkene, heterocycloalkane or heterocycloalkene;

$R^9$ is heteroarene which is unfused or fused with benzene, heteroarene, cycloalkane, cycloalkene, heterocycloalkane or heterocycloalkene;

$R^{10}$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^{11}$ is alkyl, alkenyl or alkynyl, each of which is unsubstituted or substituted with one or two of independently selected heterocycloalkyl, $CF_3$, F, Cl, Br or I; or $A^1$ and $A^2$ are taken together with the atoms to which they are attached and are benzene, cycloalkane, heteroarene or heterocycloalkane, each of which is unfused or fused with benzene, heteroarene or heterocycloalkane;

$A^3$ is H, $R^{12}$, $R^{13}$, $R^{14}$ or $R^{15}$;

$R^{12}$ is phenyl which is unfused or fused with benzene, heteroarene, cycloalkane, cycloalkene, heterocycloalkane or heterocycloalkene;

$R^{13}$ is heteroarene which is unfused or fused with benzene, heteroarene, cycloalkane, cycloalkene, heterocycloalkane or heterocycloalkene;

$R^{14}$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^{15}$ is alkyl, alkenyl or alkynyl, each of which is unsubstituted or substituted with one or two of independently selected $NH_2$, $NHW^1$, $N(W^1)_2$, phenyl, heteroaryl or heterocycloalkyl;

$W^1$ is phenyl, alkyl, alkenyl or alkynyl;

wherein each foregoing cyclic moiety is independently unsubstituted or substituted with one or two of independently selected $R^{16}$, $OR^{16}$, $SR^{16}$, $S(O)R^{16}$, $SO_2R^{16}$, $C(O)R^{16}$, $CO(O)R^{16}$, $OC(O)R^{16}$, $OC(O)OR^{16}$, $NH_2$, $NHR^{16}$, $N(R^{16})_2$, $C(O)NH_2$, $C(O)NHR^{16}$, $C(O)N(R^{16})_2$, $SO_2NH_2$, $SO_2NHR^{16}$, $SO_2N(R^{16})_2$, $CF_3$, $CF_2CF_3$, C(O)H, C(O)OH, OH, (O), $N_3$, $NO_2$, $CF_3$, $CF_2CF_3$, $OCF_3$, $OCF_2CF_3$, F, Cl, Br or I; wherein $R^{16}$ is H, $R^{17}$, $R^{18}$, $R^{19}$ or $R^{20}$;

$R^{17}$ is phenyl which is unfused or fused with benzene, heteroarene, cycloalkane, cycloalkene, heterocycloalkane or heterocycloalkene;

$R^{18}$ is heteroarene which is unfused or fused with benzene, heteroarene, cycloalkane, cycloalkene, heterocycloalkane or heterocycloalkene;

$R^{19}$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^{20}$ is alkyl, alkenyl or alkynyl, each of which is unsubstituted or substituted with one or two of independently selected $NH_2$, NH(alkyl), $N(alkyl)_2$ or $R^{21}$;

$R^{21}$ is phenyl, heteroaryl or heterocycloalkyl, each of which is unfused or fused with benzene, heteroarene or heterocycloalkane;

and wherein the moieties represented by $R^{17}$, $R^{18}$, $R^{19}$ and $R^{21}$ are unsubstituted or substituted with OH, CN, F, Cl, Br or I.

Still another embodiment comprises pharmaceutical compositions comprising a compound having formula I and an excipient.

Still another embodiment comprises methods of inhibiting Pim kinase in a mammal comprising administering thereto a therapeutically acceptable amount of a compound having formula I.

Still another embodiment comprises methods of treating cancer in a mammal comprising administering thereto a therapeutically acceptable amount of a compound having formula I

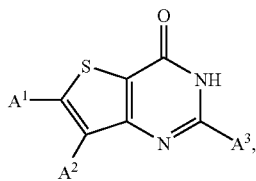

(I)

or a salt thereof, wherein $A^1$ and $A^2$ are independently selected H, $R^1$, $R^2$, $R^3$, $R^4$, OH, $OR^5$, $NH_2$, $NHR^7$, $N(R^7)_2$, F, Cl, Br or I;

$R^1$ is phenyl which is unfused or fused with benzene, heteroarene, cycloalkane, cycloalkene, heterocycloalkane or heterocycloalkene;

$R^2$ is heteroarene which is unfused or fused with benzene, heteroarene, cycloalkane, cycloalkene, heterocycloalkane or heterocycloalkene;

$R^3$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^4$ is alkyl, alkenyl or alkynyl, each of which is unsubstituted or substituted with one or two of independently selected heterocycloalkyl, $CF_3$, F, Cl, Br or I;

$R^5$ is alkyl which is unsubstituted or substituted with one or two of independently selected $R^6$, OH, $OR^7$, $NH_2$, $NHR^7$ or $N(R_7)_2$;

$R^6$ is phenyl which is unfused or fused with benzene, heteroarene, cycloalkane, cycloalkene, heterocycloalkane or heterocycloalkene;

$R^7$ is H, $R^8$, $R^9$, $R^{10}$ or $R^{11}$;

$R^8$ is phenyl which is unfused or fused with benzene, heteroarene, cycloalkane, cycloalkene, heterocycloalkane or heterocycloalkene;

$R^9$ is heteroarene which is unfused or fused with benzene, heteroarene, cycloalkane, cycloalkene, heterocycloalkane or heterocycloalkene;

$R^{10}$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^{11}$ is alkyl, alkenyl or alkynyl, each of which is unsubstituted or substituted with one or two of independently selected heterocycloalkyl, $CF_3$, F, Cl, Br or I; or $A^1$ and $A^2$ are taken together with the atoms to which they are attached and are benzene, cycloalkane, heteroarene or heterocycloalkane, each of which is unfused or fused with benzene, heteroarene or heterocycloalkane;

$A^3$ is H, $R^{12}$, $R^{13}$, $R^{14}$ or $R^{15}$;

$R^{12}$ is phenyl which is unfused or fused with benzene, heteroarene, cycloalkane, cycloalkene, heterocycloalkane or heterocycloalkene;

$R^{13}$ is heteroarene which is unfused or fused with benzene, heteroarene, cycloalkane, cycloalkene, heterocycloalkane or heterocycloalkene;

$R^{14}$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^{15}$ is alkyl, alkenyl or alkynyl, each of which is unsubstituted or substituted with one or two of independently selected $NH_2$, $NHW^1$, $N(W^1)_2$, phenyl, heteroaryl or heterocycloalkyl;

$W^1$ is phenyl, alkyl, alkenyl or alkynyl;

wherein each foregoing cyclic moiety is independently unsubstituted or substituted with one or two of independently selected $R^{16}$, $OR^{16}$, $SR^{16}$, $S(O)R^{16}$, $SO_2R^{16}$, $C(O)R^{16}$, $CO(O)R^{16}$, $OC(O)R^{16}$, $OC(O)OR^{16}$, $NH_2$, $NHR^{16}$, $N(R^{16})_2$, $C(O)NH_2$, $C(O)NHR^{16}$, $C(O)N(R^{16})_2$, $SO_2NH_2$, $SO_2NHR^{16}$, $SO_2N(R^{16})_2$, $CF_3$, $CF_2CF_3$, C(O)H, C(O)OH, OH, (O), $N_3$, $NO_2$, $CF_3$, $CF_2CF_3$, $OCF_3$, $OCF_2CF_3$, F, Cl, Br or I; wherein $R^{16}$ is H, $R^{17}$, $R^{18}$, $R^{19}$ or $R^{20}$;

$R^{17}$ is phenyl which is unfused or fused with benzene, heteroarene, cycloalkane, cycloalkene, heterocycloalkane or heterocycloalkene;

$R^{18}$ is heteroarene which is unfused or fused with benzene, heteroarene, cycloalkane, cycloalkene, heterocycloalkane or heterocycloalkene;

$R^{19}$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^{20}$ is alkyl, alkenyl or alkynyl, each of which is unsubstituted or substituted with one or two of independently selected $NH_2$, NH(alkyl), $N(alkyl)_2$ or $R^{21}$;

$R^{21}$ is phenyl, heteroaryl or heterocycloalkyl, each of which is unfused or fused with benzene, heteroarene or heterocycloalkane;

and wherein the moieties represented by $R^{17}$, $R^{18}$, $R^{19}$ and $R^{21}$ are unsubstituted or substituted with OH, CN, F, Cl, Br or I.

Still another embodiment comprises methods for decreasing tumor volume in a mammal comprising administering thereto a therapeutically acceptable amount of a compound having formula I

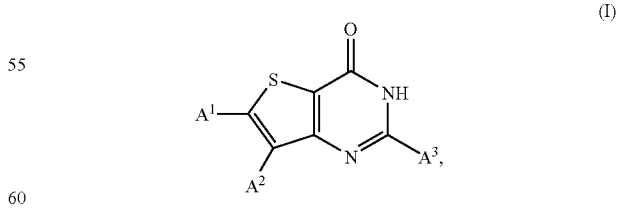

(I)

or a salt thereof, wherein $A^1$ and $A^2$ are independently selected H, $R^1$, $R^2$, $R^3$, $R^4$, OH, $OR^5$, $NH_2$, $NHR^7$, $N(R^7)_2$, F, Cl, Br or I;

$R^1$ is phenyl which is unfused or fused with benzene, heteroarene, cycloalkane, cycloalkene, heterocycloalkane or heterocycloalkene;

R² is heteroarene which is unfused or fused with benzene, heteroarene, cycloalkane, cycloalkene, heterocycloalkane or heterocycloalkene;

R³ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

R⁴ is alkyl, alkenyl or alkynyl, each of which is unsubstituted or substituted with one or two of independently selected heterocycloalkyl, $CF_3$, F, Cl, Br or I;

R⁵ is alkyl which is unsubstituted or substituted with one or two of independently selected R⁶, OH, OR⁷, $NH_2$, $NHR^7$ or $N(R_7)_2$;

R⁶ is phenyl which is unfused or fused with benzene, heteroarene, cycloalkane, cycloalkene, heterocycloalkane or heterocycloalkene;

R⁷ is H, R⁸, R⁹, R¹⁰ or R¹¹;

R⁸ is phenyl which is unfused or fused with benzene, heteroarene, cycloalkane, cycloalkene, heterocycloalkane or heterocycloalkene;

R⁹ is heteroarene which is unfused or fused with benzene, heteroarene, cycloalkane, cycloalkene, heterocycloalkane or heterocycloalkene;

R¹⁰ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

R¹¹ is alkyl, alkenyl or alkynyl, each of which is unsubstituted or substituted with one or two of independently selected heterocycloalkyl, $CF_3$, F, Cl, Br or I; or A¹ and A² are taken together with the atoms to which they are attached and are benzene, cycloalkane, heteroarene or heterocycloalkane, each of which is unfused or fused with benzene, heteroarene or heterocycloalkane;

A³ is H, R¹², R¹³, R¹⁴ or R¹⁵;

R¹² is phenyl which is unfused or fused with benzene, heteroarene, cycloalkane, cycloalkene, heterocycloalkane or heterocycloalkene;

R¹³ is heteroarene which is unfused or fused with benzene, heteroarene, cycloalkane, cycloalkene, heterocycloalkane or heterocycloalkene;

R¹⁴ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

R¹⁵ is alkyl, alkenyl or alkynyl, each of which is unsubstituted or substituted with one or two of independently selected $NH_2$, $NHW^1$, $N(W^1)_2$, phenyl, heteroaryl or heterocycloalkyl;

W¹ is phenyl, alkyl, alkenyl or alkynyl;

wherein each foregoing cyclic moiety is independently unsubstituted or substituted with one or two of independently selected $R^{16}$, $OR^{16}$, $SR^{15}$, $S(O)R^{16}$, $SO_2R^{16}$, $C(O)R^{16}$, $CO(O)R^{16}$, $OC(O)R^{16}$, $OC(O)OR^{16}$, $NH_2$, $NHR^{16}$, $N(R^{16})_2$, $C(O)NH_2$, $C(O)NHR^{16}$, $C(O)N(R^{16})_2$, $SO_2NH_2$, $SO_2NHR^{16}$, $SO_2N(R^{16})_2$, $CF_3$, $CF_2CF_3$, C(O)H, C(O)OH, OH, (O), $N_3$, $NO_2$, $CF_3$, $CF_2CF_3$, $OCF_3$, $OCF_2CF_3$, F, Cl, Br or I; wherein R¹⁶ is H, R¹⁷, R¹⁸, R¹⁹ or R²⁰;

R¹⁷ is phenyl which is unfused or fused with benzene, heteroarene, cycloalkane, cycloalkene, heterocycloalkane or heterocycloalkene;

R¹⁸ is heteroarene which is unfused or fused with benzene, heteroarene, cycloalkane, cycloalkene, heterocycloalkane or heterocycloalkene;

R¹⁹ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

R²⁰ is alkyl, alkenyl or alkynyl, each of which is unsubstituted or substituted with one or two of independently selected $NH_2$, NH(alkyl), $N(alkyl)_2$ or R²¹;

R²¹ is phenyl, heteroaryl or heterocycloalkyl, each of which is unfused or fused with benzene, heteroarene or heterocycloalkane;

and wherein the moieties represented by R¹⁷, R¹⁸, R¹⁹ and R²¹ are unsubstituted or substituted with OH, CN, F, Cl, Br or I.

Still another embodiment comprises a method of treating leukemia, colon cancer, glioblastomas, lymphomas, melanomas, carcinomas of the breast or cervical carcinomas in a mammal comprising administering thereto a therapeutically acceptable amount of a compound having formula I.

Still another embodiment comprises methods for potentiation of cytotoxic cancer therapy in a mammal comprising administering thereto a therapeutically acceptable amount of a compound having formula I.

Still another embodiment comprises methods for potentiation of radiation therapy in a mammal comprising administering thereto a therapeutically acceptable amount of a compound having formula I.

Still another embodiment comprises methods of treating ischemia reperfusion injury associated with myocardial infarction, stroke, neural trauma or organ transplantation in a mammal comprising administering thereto a therapeutically acceptable amount of a compound having formula I.

Still another embodiment comprises methods of treating reperfusion of the eye, kidney, gut or skeletal muscle in a mammal comprising administering thereto a therapeutically acceptable amount of a compound having formula I.

Still another embodiment comprises methods of treating arthritis, gout, inflammatory bowel disease, CNS inflammation, multiple sclerosis, allergic encephalitis, sepsis, septic shock, hemmorhagic shock, pulmonary fibrosis or uveitis in a mammal comprising administering thereto a therapeutically acceptable amount of a compound having formula I.

Still another embodiment comprises a method of treating rheumatoid arthritis or septic shock in a mammal comprising administering thereto a therapeutically acceptable amount of a compound having formula I.

Still another embodiment comprises methods of treating diabetes or Parkinsons disease in a mammal comprising administering thereto a therapeutically acceptable amount of a compound having formula I.

Still another embodiment comprises methods of treating hypoglycemia in a mammal comprising administering thereto a therapeutically acceptable amount of a compound having formula I.

Still another embodiment comprises methods of treating retroviral infection in a mammal comprising administering thereto a therapeutically acceptable amount of a compound having formula I.

Still another embodiment comprises methods of treating liver toxicity following acetaminophen overdose in a mammal comprising administering thereto a therapeutically acceptable amount of a compound having formula I.

Still another embodiment comprises a method of treating cardiac or kidney toxicities from doxorubicin or platinum based antineoplastic agents in a mammal comprising administering thereto a therapeutically acceptable amount of a compound having formula I.

Still another embodiment comprises methods of treating skin damage secondary to sulfur mustards in a mammal comprising administering thereto a therapeutically acceptable amount of a compound having formula I.

DETAILED DESCRIPTION OF THE INVENTION

Variable moieties of compounds herein are represented by identifiers (capital letters with numerical and/or alphabetical superscripts) and may be specifically embodied.

It is meant to be understood that proper valences are maintained for all combinations herein, that monovalent moieties having more than one atom are attached through their left ends.

It is also meant to be understood that a specific embodiment of a variable moiety may be the same or different as another specific embodiment having the same identifier.

The term "alkenyl," as used herein, means monovalent, straight or branched chain hydrocarbon moieties having one or more than one carbon-carbon double bonds, such as $C_2$-alkenyl, $C_3$-alkenyl, $C_4$-alkenyl, $C_5$-alkenyl, $C_6$-alkenyl and the like.

The term "alkyl," as used herein, means monovalent, saturated, straight or branched chain hydrocarbon moieties, such as $C_1$-alkyl, $C_2$-alkyl, $C_3$-alkyl, $C_4$-alkyl, $C_5$-alkyl, $C_6$-alkyl and the like.

The term "alkynyl," as used herein, means monovalent, straight or branched chain hydrocarbon moieties having one or more than one carbon-carbon triple bonds, such as $C_2$-alkynyl, $C_3$-alkynyl, $C_4$-alkynyl, $C_5$-alkynyl, $C_6$-alkynyl and the like.

The term "cycloalkane," as used herein, means saturated cyclic or bicyclic hydrocarbon moieties, such as $C_4$-cycloalkane, $C_5$-cycloalkane, $C_6$-cycloalkane, $C_7$-cycloalkane, $C_8$-cycloalkane, $C_9$-cycloalkane, $C_{10}$-cycloalkane, $C_{11}$-cycloalkane, $C_{12}$-cycloalkane and the like.

The term "cycloalkyl," as used herein, means monovalent, saturated cyclic and bicyclic hydrocarbon moieties, such as $C_3$-cycloalkyl, $C_4$-cycloalkyl, $C_5$-cycloalkyl, $C_6$-cycloalkyl, $C_7$-cycloalkyl, $C_8$-cycloalkyl, $C_9$-cycloalkyl, $C_{10}$-cycloalkyl, $C_{11}$-cycloalkyl, $C_{12}$-cycloalkyl and the like.

The term "cycloalkene," as used herein, means cyclic and bicyclic hydrocarbon moieties having one or more than one carbon-carbon double bonds, such as $C_5$-cycloalkene, $C_6$-cycloalkene, $C_7$-cycloalkene, $C_8$-cycloalkene, $C_9$-cycloalkene, $C_{10}$-cycloalkene, $C_{11}$-cycloalkene, $C_{12}$-cycloalkene and the like.

The term "cycloalkenyl," as used herein, means monovalent, cyclic hydrocarbon moieties having one or more than one carbon-carbon double bonds, such as $C_4$-cycloalkenyl, $C_5$-cycloalkenyl, $C_6$-cycloalkenyl, $C_7$-cycloalkenyl, $C_8$-cycloalkenyl, $C_9$-cycloalkenyl, $C_{10}$-cycloalkenyl, $C_{11}$-cycloalkenyl, $C_{12}$-cycloalkenyl and the like.

The term "heteroarene," as used herein, means furan, imidazole, isothiazole, isoxazole, 1,2,3-oxadiazole, 1,2,5-oxadiazole, 1,3,4-oxadiazole, oxazole, pyrazine, pyrazole, pyridazine, pyridine, pyrimidine, pyrrole, thiazole, 1,3,4-thiadiazole, thiophene, triazine and 1,2,3-triazole.

The term "heteroaryl," as used herein, means furanyl, imidazolyl, isothiazolyl, isoxazolyl, 1,2,3-oxadiazoyl, 1,2,5-oxadiazolyl, 1,3,4-oxadiazolyl, oxazolyl, pyrazinyl, pyrazolyl, pyridazinyl, pyridinyl, pyrimidinyl, pyrrolyl, tetrazolyl, thiazolyl, 1,2,3-thiadiazoyl, 1,2,5-thiadiazolyl, 1,3,4-thiadiazolyl, thiophenyl, triazinyl and 1,2,3-triazolyl.

The term "heterocycloalkane," as used herein, means cycloalkane having one or two or three $CH_2$ moieties replaced with independently selected O, S, S(O), $SO_2$ or NH and one or two CH moieties unreplaced or replaced with N and also means cycloalkane having one or two or three $CH_2$ moieties unreplaced or replaced with independently selected O, S, S(O), $SO_2$ or NH and one or two CH moieties replaced with N.

The term "heterocycloalkene," as used herein, means cycloalkene having one or two or three $CH_2$ moieties replaced with independently selected O, S, S(O), $SO_2$ or NH and one or two CH moieties unreplaced or replaced with N and also means cycloalkene having one or two or three $CH_2$ moieties unreplaced or replaced with independently selected O, S, S(O), $SO_2$ or NH and one or two CH moieties replaced with N.

The term "heterocycloalkyl," as used herein, means cycloalkyl having one or two or three $CH_2$ moieties replaced with independently selected O, S, S(O), $SO_2$ or NH and one or two CH moieties unreplaced or replaced with N and also means cycloalkyl having one or two or three $CH_2$ moieties unreplaced or replaced with independently selected O, S, S(O), $SO_2$ or NH and one or two CH moieties replaced with N.

The term "heterocycloalkenyl," as used herein, means cycloalkenyl having one or two or three $CH_2$ moieties replaced with independently selected O, S, S(O), $SO_2$ or NH and one or two CH moieties unreplaced or replaced with N and also means cycloalkenyl having one or two or three $CH_2$ moieties unreplaced or replaced with independently selected O, S, S(O), $SO_2$ or NH and one or two CH moieties replaced with N.

The term "cyclic moiety," as used herein, means benzene, cycloalkane, cycloalkyl, cycloalkene, cycloalkenyl, heteroarene, heteroaryl, heterocycloalkane, heterocycloalkyl, heterocycloalkene, heterocycloalkenyl and phenyl.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures, relative and absolute diastereoisomers and the compounds thereof.

Compounds of this invention may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds of this invention may also exist as a mixture of "Z" and "E" isomers.

Compounds of this invention containing NH, C(O)H, C(O)OH, $C(O)NH_2$, OH or SH moieties may have attached thereto prodrug-forming moieties. The prodrug-forming moieties are removed by metabolic processes and release the compounds having the freed NH, C(O)H, C(O)OH, $C(O)NH_2$, OH or SH in vivo. Prodrugs are useful for adjusting such pharmacokinetic properties of the compounds as solubility and/or hydrophobicity, absorption in the gastrointestinal tract, bioavailability, tissue penetration, and rate of clearance.

Metabolites of compounds having Formula I, produced by in vitro or in vivo metabolic processes, may also have utility for treating diseases caused or exacerbated by an unregulated or overexpressed Pim kinase.

Certain precursor compounds of compounds having Formula I may be metabolized in vitro or in vivo to form compounds having Formula I and may thereby also have utility for treating diseases caused or exacerbated by an unregulated or overexpressed Pim kinase.

Compounds having Formula I may exist as acid addition salts, basic addition salts or zwitterions. Salts of compounds having Formula I are prepared during their isolation or following their purification. Acid addition salts are those derived from the reaction of a compound having Formula I with acid. Accordingly, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of the compounds having Formula I are meant to be embraced by this invention. Basic addition salts of compounds are those derived from the reaction of the compounds having Formula I with the bicarbonate, carbonate, hydroxide, or phosphate of cations such as lithium, sodium, potassium, calcium and magnesium.

Compounds having Formula I may be administered, for example, bucally, ophthalmically, orally, osmotically, parenterally (intramuscularly, intraperintoneally intrasternally, intravenously, subcutaneously), rectally, topically, transdermally and vaginally.

Therapeutically effective amounts of a compound having Formula I depend on recipient of treatment, disease treated and severity thereof, composition comprising it, time of administration, route of administration, duration of treatment, potency, rate of clearance and whether or not another drug is co-administered. The amount of a compound having Formula I used to make a composition to be administered daily to a patient in a single dose or in divided doses is from about 0.001 to about 200 mg/kg body weight. Single dose compositions contain these amounts or a combination of submultiples thereof.

Compounds having Formula I may be administered with or without an excipient. Excipients include, for example, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Compounds having Formula I may be radiolabeled with a radioactive isotope such as carbon (i.e. $^{13}C$), hydrogen (i.e. $^{3}H$), nitrogen (i.e. $^{15}N$), phosphorus (i.e. $^{32}P$), sulfur (i.e. $^{35}S$), iodide (i.e. $^{125}I$) and the like. Radioactive isotopes may be incorporated into the compounds having Formula I by reacting the same and a radioactive derivitizing agent or by incorporating a radiolabeled intermediate into their syntheses. The radiolabeled compounds of Formula I are useful for both prognostic and diagnostic applications and for in vivo and in vitro imaging.

Compounds having Formula I may be incorporated into devices such as, but not limited to, arterio-venous grafts, billiary stents, by-pass grafts, catheters, central nervous system shunts, coronary stents, drug delivery balloons, peripheral stents and uretural stents, each of which may be used in areas such as, but not limited to, the vasculature for introduction of a compound having Formula I into selected tissues or organs in the body. One measure of the effectiveness of compounds having Formula I is reduction or elimination of device-associated thrombi and complications associated therewith.

Compounds having Formula I can used as a radiosensitizers which enhance the efficacy of radiotherapy. Examples of radiotherapy include, but are not limited to, external beam radiotherapy, teletherapy, brachtherapy and sealed and unsealed source radiotherapy.

Excipients for preparation of compositions comprising a compound having Formula I to be administered orally include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water and mixtures thereof. Excipients for preparation of compositions comprising a compound having Formula I to be administered ophthalmically or orally include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound having Formula I to be administered osmotically include, for example, chlorofluoro-hydrocarbons, ethanol, water and mixtures thereof. Excipients for preparation of compositions comprising a compound having Formula I to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound having Formula I to be administered rectally or vaginally include, for example, cocoa butter, polyethylene glycol, wax and mixtures thereof.

Compounds having formula I are also expected to be useful when used with alkylating agents, angiogenesis inhibitors, antibodies, antimetabolites, antimitotics, antiproliferatives, aurora kinase inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors inhibitors, hormonal therapies, immunologicals, intercalating antibiotics, kinase inhibitors, mammalian target of rapomycin inhibitors, mitogen-activated extracellular signal-regulated kinase inhibitors, non-steroidal anti-inflammatory drugs (NSAID's), platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

Alkylating agents include altretamine, AMD-473, AP-5280, apaziquone, bendamustine, brostallicin, busulfan, carboquone, carmustine (BCNU), chlorambucil, Cloretazine™ (VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, treosulfan, trofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs vascular endothelial growth factor receptor tyrosine kinase (VEGFR) inhibitors and the like.

Aurora kinase inhibitors include AZD-1152, MLN-8054, VX-680 and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX™ (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFr immunoliposomes, EGF-vaccine, EMD-7200, ERBITUX (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), Herceptin® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB®, NCS-683664, PU24FCl, PU-3, radicicol, SNX-2112, STA-9090 VER49009 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam) ibuprofin cream, ALEVE® and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin and the like.

Polo-like kinase inhibitors include BI-2536 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™, axitinib (AG-13736), AZD-2171, CP-547,632, IM-862, Macugen (pegaptamib), NEXAVAR® (sorafenib, BAY43-9006), pazopanib (GW-786034), (PTK-787, ZK-222584), SUTENT® (sunitinib, SU-11248), VEGF trap, vatalanib, ZACTIMA™ (vandetanib, ZD-6474) and the like.

Antimetabolites include ALIMTA® (premetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR, enocitabine, ethnylcytidine, fludarabine, hydroxyurea, 5-fluorouracil (5-FU) alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosate, pelitrexol, pentostatin, raltitrexed, Ribavirin, triapine, trimetrexate, S-1, tiazofurin, tegafur, TS-1, vidarabine, UFT and the like.

Antibiotics include intercalating antibiotics aclarubicin, actinomycin D, amrubicin, annamycin, adriamycin, BLENOXANE® (bleomycin), daunorubicin, CAELYX® or MYOCET® (doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab and and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), fadrozole, FARESTON® (toremifene), FASLODEX® (fulvestrant), FEMARA®, (letrozole), formestane, glucocorticoids, HECTOROL® or RENAGEL® (doxercalciferol), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), predisone, PROPECIA® (finasteride), rilostane, SUPREFACT® (buserelin), TRELSTAR® (luteinizing hormone releasing hormone (LHRH)), vantas, VETORYL®, (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN®

(aliretinoin), ATRAGEN® (liposomal tretinoin), TARGRETIN® (bexarotene), LGD-1550 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-n1, combinations thereof and the like. Other agents include ALFAFERONE®, BAM-002, BEROMUN® (tasonermin), BEXXAR® (tositumomab), CamPath® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010, melanoma vaccine, mitumomab, molgramostim, MYLOTARG™ (gemtuzumab ozogamicin), NEUPOGEN® (filgrastim), OncoVAC-CL, OvaRex® (oregovomab), pemtumomab (Y-muHMFG1), PROVENGE®, sargaramostim, sizofilan, teceleukin, TheraCys®, ubenimex, VIRULIZIN®, Z-100, WF-10, PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include include krestin, lentinan, sizofiran, picibanil PF-3512676 (CpG-8954), ubenimex and the like.

Pyrimidine analogs include cytarabine (ara C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881, vinflunine, ZK-EPO and the like.

Compounds of the present invention are also intended to be used as a radiosensitizer that enhances the efficacy of radiotherapy. Examples of radiotherapy include, but are not limited to, external beam radiotherapy, teletherapy, brachtherapy and sealed and unsealed source radiotherapy.

Additionally, compounds having formula I may be combined with other chemptherapeutic agents such as ABRAXANE™ (ABI-007), ABT-100 (farnesyl transferase inhibitor), ADVEXIN®, ALTOCOR® or MEVACOR® (lovastatin), AMPLIGEN® (poly I:poly C12U, a synthetic RNA), APTOSYN™ (exisulind), AREDIA® (pamidronic acid), arglabin, L-asparaginase, atamestane (1-methyl-3,17-dione-androsta-1,4-diene), AVAGE® (tazarotne), AVE-8062, BEC2 (mitumomab), cachectin or cachexin (tumor necrosis factor), canvaxin (vaccine), CeaVac™ (cancer vaccine), CELEUK® (celmoleukin), CEPLENE® (histamine dihydrochloride), CERVARIX™ (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CyPat™, combrestatin A4P, DAB(389)EGF or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906, GARDASIL® (quadrivalent human papillomavirus (Types 6, 11, 16, 18) recombinant vaccine), gastrimmune, genasense, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), OncoVAX (IL-2 Vaccine), ORATHECIN™ (rubitecan), OSIDEM® (antibody-based cell drug), OvaRex® MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), Taxoprexin® (DHA-paclitaxel), TELCYTA™ (TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFerade™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS™ (trabectedin), ZD-6126, ZINECARD® (dexrazoxane), zometa (zolendronic acid), zorubicin and the like.

It is expected that compounds having formula I would also inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Pim Kinase Assays.

Kinase assays were conducted as follows with final concentrations as listed. In 384-well v-bottom polypropylene plates, 10 µl compound (2% DMSO), was mixed with 20 µl of Pim1 (50 pM), Pim2 (500 pM), or Pim3 (300 pM) and peptide substrate (biotin-C$_6$linker-VRRLRRLTAREAA) (2 µM), followed by immediate initiation with 20 µl λ-[$^{33}$P]-ATP (5 µM, 2 mCi/µmol) using a reaction buffer comprising 25 mM HEPES, pH 7.5, 0.5 mM DTT, 1 mM MgCl$_2$, 100 µM Na$_3$VO$_4$, 0.075 mg/ml Triton X-100. Reactions were quenched after 1 hr by the addition of 50 µl stop buffer (50 mM EDTA, 2M NaCl). 80 μL of the stopped reactions were transferred to 384-well streptavidin-coated plates (FlashPlate Plus, Perkin Elmer), incubated 30 minutes at RT and washed 3 times with 0.05% Tween-20/PBS using an ELX-405 automated plate washer (BioTek), and counted on a TopCount Scintillation Plate Reader (Packard).

All of the examples tested demonstrated Pim kinase inhibitory activity.

As Pim kinase inhibitors, the compounds of this invention have numerous therapeutic applications related to ischemia reperfusion injury, inflammatory diseases, degenerative diseases, protection from adverse effects of cytotoxic compounds, and potentiation of cytotoxic cancer therapy. In particular, compounds of this invention potentiate radiation and chemotherapy by increasing cell death of cancer cells, limiting tumor growth, decreasing metastasis, and prolonging the survival of tumor-bearing mammals. Compounds having formula I can treat leukemia, colon cancer, glioblastomas, lymphomas, melanomas, carcinomas of the breast, and cervical carcinomas.

Other therapeutic applications include retroviral infection, arthritis, gout, inflammatory bowel disease, CNS inflammation, multiple sclerosis, allergic encephalitis, sepsis, septic shock, hemmorhagic shock, pulmonary fibrosis, uveitis, diabetes, Parkinsons disease, myocardial infarction, stroke, other neural trauma, organ transplantation, reperfusion of the eye, reperfusion of the kidney, reperfusion of the gut, reperfusion of skeletal muscle, liver toxicity following acetomiphen overdose, cardiac and kidney toxicities from doxorubicin and platinum based antineoplastic agents, and skin damage secondary to sulfur mustards.

The following examples are presented to provide what is believed to be the most useful and readily understood description of procedures and conceptual aspects of this invention.

Example 1

8-bromo-2-[(3-hydroxyphenylamino)methyl]-3H-benzo[4,5]thieno[3,2-d]pyrimidin-4-one Example 1A methyl 3-amino-5-bromobenzo[b]thiophene-2-carboxylate To a solution of 5-bromo-2-fluorobenzonitrile (13.5 g, 67.5 mmol) in N,N-dimethylformamide at 0° C. was added methyl 2-mercaptoacetate (6.45 mL, 70.88 mmol). The mixture was stirred at 0° C. for 30 minutes and 5N sodium hydroxide (20.25 mL) added. After stirring at 0° C. for 3 hours, the mixture was quenched with ice-water and the resulting precipitate collected by filtration and dried to give 18.5 g (96%) of a white solid. LCMS (APCI) m/z: 287(M+H)$^+$.

Example 1B methyl 3-(1-amino-2-chloroethylideneamino)-5-bromobenzo[b]thiophene-2-carboxylate A suspension of EXAMPLE 1A (7.2 g, 25.16 mmol) in 4N hydrochloric acid in dioxane (70 mL) was treated with 2-chloroacetonitrile (3.18 mL, 50.32 mmol) at ambient temperature for 3 hours. The white solid was collected by filtration and dried to give the title compound as the hydrochloride salt. LCMS (APCI) m/z: 362(M+H)$^+$.

Example 1C 8-bromo-2-[(3-hydroxyphenylamino)methyl]-3H-benzo[4,5]thieno[3,2-d]pyrimidin-4-one A mixture of EXAMPLE 1B (30 mg, 0.076 mmol) and 3-aminophenol (41 mg, 0.38 mmol) in N,N-dimethylformamide (2 mL) was stirred at ambient temperature overnight and concentrated. The residue was purified by reverse phase HPLC (SymmetryPrep Shield RP18 prep cartridge, 0-70% gradient of acetonitrile/water containing 0.1% trifluoroacetic acid) to provide the title compound as the trifluoroacetate salt (56% yield). $^1$H NMR (DMSO-d$_6$) δ 4.31 (d, J=5.8, Hz, 2H), 6.00-6.05 (m, 2H), 6.11 (t, J=2.1 Hz, 1H), 6.15 (dd, J=7.9, 1.5 Hz, 1H), 6.87 (t, J=7.9 Hz, 1H), 7.82 (dd, J=8.7, 2.0 Hz, 1H), 8.15 (d, J=8.8 Hz, 1H), 8.40 (d, J=1.8 Hz, 1H), 9.02 (s, 1H), 12.76 (s, br, 1H).

Example 2

8-chloro-2-(2-piperidin-1-ylethyl)-3H-benzo[4,5]thieno[3,2-d]pyrimidin-4-one

Example 2A methyl 3-amino-5-chlorobenzo[b]thiophene-2-carboxylate

The title compound was prepared as described in EXAMPLE 1A using 5-chloro-2-fluorobenzonitrile in place of 5-bromo-2-fluorobenzonitrile (95% yield). $^1$H NMR (DMSO-d$_6$) δ 3.79 (s, 3H), 7.16 (s, 2H), 7.54 (dd, J=8.7, 2.0 Hz, 1H), 7.88 (d, J=8.6 Hz, 1H), 8.30 (d, J=2.2 Hz, 1H).

Example 2B methyl 3-(1-amino-3-chloropropylideneamino)-5-chlorobenzo[b]thiophene-2-carboxylate The title compound was prepared as described in EXAMPLE 1B using EXAMPLE 2A in place of EXAMPLE 1A and 3-chloropropionitrle in place of 2-chloroacetonitrile (90% yield). LCMS (APCI) m/z: 332 (M+H)$^+$.

Example 2C 8-chloro-2-(2-piperidin-1-ylethyl)-3H-benzo[4,5]thieno[3,2-d]pyrimidin-4-one The title compound as the trifluoroacetate salt was prepared as described in EXAMPLE 1C using EXAMPLE 2B in place of EXAMPLE 1B and piperidine in place of 3-aminophenol (83% yield). $^1$H NMR (DMSO-d$_6$) δ 1.43 (q, J=11.5 Hz, 1H), 1.58-1.75 (m, 3H), 1.87 (d, J=13.7 Hz, 2H), 2.95-3.10 (m, 2H), 3.23 (t, J=7.3 Hz, 2H), 3.57 (d, J=11.6 Hz, 2H), 3.65 (t, J=6.3 Hz, 2H), 7.73 (dd, J=8.5, 2.1 Hz, 1H), 8.24 (d, J=8.5 Hz, 1H), 8.25 (s, 1H), 9.18 (s, 1H), 13.01 (s, 1H).

Example 3

2-dimethylaminomethyl-8-pyrrolidin-1-yl-3H-benzo[4,5]thieno[3,2-d]pyrimidin-4-one Example 3A 8-bromo-2-dimethylaminomethyl-3H-benzo[4,5]thieno[3,2-d]pyrimidin-4-one The title compound was prepared as described in EXAMPLE 1C using dimethylamine in place of 3-aminophenol (92% yield). $^1$H NMR (methanol-d$_4$) δ 3.17 (s, 6H), 4.56 (s, 2H), 7.79 (dd, J=8.7, 2.0 Hz, 1H), 8.00 (d, J=8.5 Hz, 1H), 8.56 (d, J=1.8 Hz, 1H).

Example 3B

2-dimethylaminomethyl-8-pyrrolidin-1-yl-3H-benzo[4,5]thieno[3,2-d]pyrimidin-4-one To a mixture of biphenyl-2-yldi-tert-butylphosphine (5.3 mg, 0.018 mmol), tris(dibenzylidineacetone)dipalladium(0) (4.1 mg, 0.0044 mmol) and sodium tert-butoxide (26 mg, 0.27 mmol) in toluene (2.5 mL) was added EXAMPLE 3A (30 mg, 0.089 mmol) and pyrrolidine (0.015 mL, 0.18 mmol). The mixture was heated at 120° C. for 20 minutes in a CEM microwave synthesizer and concentrated. The residue was purified by reverse phase HPLC on a C18 column using a gradient of 0-70% acetonitrile/0.1% TFA in water to give the title compound as the trifluoroacetate salt (25.6 mg, 52%). $^1$H NMR (DMSO-d$_6$) δ 1.98-2.06 (m, 4H), 3.02 (s, 6H), 3.34 (t, J=6.4 Hz, 4H), 4.48 (s, 2H), 7.06 (dd, J=8.8, 2.4 Hz, 1H), 7.32 (d, J=2.4 Hz, 1H), 7.91 (d, J=8.8 Hz, 1H), 10.05 (s, 1H), 13.04 (s, 1H).

Example 4

2-dimethylaminomethyl-8-(4-hydroxyphenyl)-3H-benzo[4,5]thieno[3,2-d]pyrimidin-4-one To a mixture EXAMPLE 3A (40 mg, 0.11 mmol), dichloro bis(triphenylphosphine) palladium(II) (8.3 mg, 0.012 mmol) and 4-hydroxyphenyl boronic acid (19.9 mg, 0.14 mmol) in 2.5 mL of a 7:2:3 mixture of 1,2-dimethoxyethane/ethanol/water was added 1M sodium carbonate (0.2 mL) and the mixture heated for 600 seconds in a CEM microwave synthesizer. After concentration, the residue was purified by reverse phase HPLC on a C18 column using a gradient of 0-70% acetonitrile/0.1% TFA in water to give the title compound as the trifluoroacetate salt (33 mg, 65%). To a solution of the trifluoroacetate salt in methanol was added excess 1N hydrochloric acid in ether and the mixture stirred at ambient temperature for 4 hours. The white precipitate was collected and dried to give the title compound as the hydrochloride salt. $^1$H NMR (DMSO-d$_6$) δ 3.02 (s, 6H), 4.52 (s, 2H), 6.94 (d, J=8.5 Hz, 2H), 7.63 (d, J=8.5 Hz, 2H), 7.93 (dd, J=8.5, 1.8 Hz, 1H), 8.21 (d, J=8.5 Hz, 1H), 8.52 (d, J=1.5 Hz, 1H), 9.73 (s, 1H), 10.36 (s, br, 1H), 13.23 (s, br, 1H).

Example 5

2-dimethylaminomethyl-8-((E)-pent-1-enyl)-3H-benzo[4,5]thieno[3,2-d]pyrimidin-4-one The title compound was prepared as the trifluoroacetate salt as described in EXAMPLE 4 using (E)-4,4,5,5-tetramethyl-2-(pent-1-enyl)-1,3,2-dioxaborolane in place of 4-hydroxyphenyl boronic acid (83% yield). $^1$H NMR (DMSO-d$_6$) δ 0.96 (t, J=7.4 Hz, 3H), 1.45-1.56 (m, 2H), 2.24 (q, J=6.7 Hz, 2H), 3.04 (s, 6H), 4.50 (s, 2H), 6.41-6.52 (m, 1H), 6.58-6.64 (m, 1H), 7.79 (dd, J=8.6, 1.8 Hz, 1H), 8.11 (d, J=8.6 Hz, 1H), 8.25 (d, J=1.2 Hz, 1H), 10.11 (s, 1H), 13.15 (s, 1H).

Example 6

2-((S)-3-hydroxypyrrolidin-1-ylmethyl)-8-thiophen-3-yl-3H-benzo[4,5]thieno[3,2-d]pyrimidin-4-one

Example 6A

8-bromo-2-((S)-3-hydroxypyrrolidin-1-ylmethyl)-3H-benzo[4,5]thieno[3,2-d]pyrimidin-4-one The title compound was prepared as described in EXAMPLE 1C using (S)-pyrrolidin-3-ol in place of 3-aminophenol (90% yield). $^1$H NMR (DMSO-d$_6$) δ 1.76-2.35 (m, 2H), 3.21-4.10 (m, 4H), 4.33-4.97 (m, 3H), 5.53 (s, 1H), 7.87 (dd, J=8.7, 2.0 Hz, 1H), 8.21 (d, J=8.5 Hz, 1H), 8.51 (s, 1H), 10.43 (d, J=1.9 Hz, 1H), 13.22 (s, 1H).

Example 6B

2-((S)-3-hydroxypyrrolidin-1-ylmethyl)-8-thiophen-3-yl-3H-benzo[4,5]thieno[3,2-d]pyrimidin-4-one The title compound was prepared as the trifluoroacetate salt as described in EXAMPLE 4 using EXAMPLE 6A in place of EXAMPLE 3A and thiophen-3-ylboronic acid in place of 4-hydroxyphenyl boronic acid (63% yield). $^1$H NMR (DMSO-d$_6$) δ 1.85-2.30 (m, 2H), 3.15-4.03 (m, 4H), 4.51 (s, br, 1H), 4.63 (d, J=13.4 Hz, 2H), 5.55 (s, 1H), 7.69 (dd, J=4.9, 1.2 Hz, 1H), 7.75 (dd, J=5.0, 2.9 Hz, 1H), 8.03 (dd, J=2.9, 1.4 Hz, 1H), 8.08 (dd, J=8.5, 1.8 Hz, 1H), 8.24 (d, J=8.5 Hz, 1H), 8.56 (s, 1H), 10.43 (s, br, 1H), 13.14 (s, br, 1H).

Example 7

2-dimethylaminomethyl-8-(6-piperidin-1-yl-hex-1-ynyl)-3H-benzo[4,5]thieno[3,2-d]pyrimidin-4-one

Example 7A

8-(6-chloro-hex-1-ynyl)-2-dimethylaminomethyl-3H-benzo[4,5]thieno[3,2-d]pyrimidin-4-one To a mixture of EXAMPLE 3A (60 mg, 0.18 mmol), 6-chlorohex-1-yne (0.064 mL, 0.53 mmol), tetrakis(triphenylphosphine)palladium(0) (30.7 mg, 0.03 mmol) and triethylamine (0.074 mL, 0.53 mmol) in N,N-dimethylformamide (3 mL) was added copper(I) iodide (6.8 mg, 0.036 mmol) and the mixture heated at 100° C. for 600 seconds in a CEM microwave synthesizer. After concentration, the residue was purified by reverse phase HPLC on a C18 column using a gradient of 0-70% acetonitrile/0.1% TFA in water to give the title compound as the trifluoroacetate salt (57 mg, 65%). $^1$H NMR (DMSO-d$_6$) δ 1.62-1.79 (m, 2H), 1.83-1.98 (m, 2H), 2.54 (t, J=7.2 Hz, 2H), 3.03 (s, 6 H), 3.72 (t, J=6.4 Hz, 2H), 4.50 (s, 2H), 7.67 (dd, J=8.4, 1.7 Hz, 1H), 8.18 (d, J=8.3 Hz, 1H), 8.37 (d, J=1.2 Hz, 1H), 9.82 (s, 1H), 13.20 (s, 1H).

Example 7B

2-dimethylaminomethyl-8-(6-piperidin-1-yl-hex-1-ynyl)-3H-benzo[4,5]thieno[3,2-d]pyrimidin-4-one EXAMPLE 7A (10 mg, 0.021 mmol) in piperidine (1.5 mL) was heated at 80° C. for 1 hour. The mixture was concentrated and the residue purified by reverse phase HPLC on a C18 column using a gradient of 0-70% acetonitrile/0.1% TFA in water to give the title compound as the trifluoroacetate salt (11.5 mg, 85%). $^1$H NMR (DMSO-d$_6$) δ 1.32-1.49 (m, 1H), 1.55-1.74 (m, 5H), 1.75-1.89 (m, 4H), 2.55 (t, J=7.2 Hz, 2H), 2.82-2.94 (m, 2H) 3.03 (s, 6H), 3.06-3.13 (m, 2H), 3.40-3.62 (m, 2H), 4.50 (s, 2H), 7.67 (dd, J=8.5, 1.8 Hz, 1H), 8.20 (d, J=8.5 Hz, 1H), 8.36 (d, J=1.2 Hz, 1H), 9.29 (s, 1H), 10.11 (s, br, 1H), 13.24 (s, br, 1H).

Example 8

7-(1H-indol-5-yl)-6-phenylthieno[3,2-d]pyrimidin-4 (3H)-one

Example 8A methyl 3-amino-4-bromo-5-phenylthiophene-2-carboxylate

To a mixture of methyl 3-amino-5-phenylthiophene-2-carboxylate (2.33 g, 10 mmol) and phenyltrimethylammonium tribromide (9.4 g, 25 mmol) in dichloromethane (25 mL) and methanol (25 mL) was added calcium carbonate (4.03 g, 40 mmol) and the mixture stirred overnight. The solid was filtered off and the filtrate concentrated. The residue was purified by flash chromatography on silica gel using 1:10 ethyl acetate/hexanes to give 2.75 g of the title compound. $^1$H NMR (DMSO-d$_6$) δ 7.62-7.65 (m, 2H), 7.47-7.51 (m, 3H), 3.80 (s, 3H).

Example 8B methyl 3-amino-4-(1H-indol-5-yl)-5-phenylthiophene-2-carboxylate

A mixture of EXAMPLE 8A (0.125 g, 0.4 mmol), 5-(4,4,5,5-tetramethyl-1,3,2-dioxaborolan-2-yl)-1H-indole (0.122 g, 0.5 mmol), tetrakis(triphenylphosphine) palladium(0) (22.4 mg, 0.02 mmol) and cesium fluoride (0.182 g, 1.2 mmol) in 1,2-dimethoxyethane (2 mL) and methanol (1 mL) was heated at 150° C. for 10 minutes under microwave conditions (CEM Discovery). After cooling, the mixture was purified by flash chromatography on silica gel using 3:7 ethyl acetate/hexanes to give 98 mg (71%) of the title compound. $^1$H NMR (DMSO-d$_6$) δ 11.18 (s, 1H), 7.37-7.43 (m, 3H), 7.17-7.23 (m, 5H), 6.85 (dd, J=8.3, 1.5, 1H), 6.42-6.43 (m, 1H), 5.92 (s, 2H), 3.78 (s, 3H).

Example 8C 7-(1H-indol-5-yl)-6-phenylthieno[3,2-d]pyrimidin-4 (3H)-one

A mixture of EXAMPLE 8B (95 mg, 0.27 mmol) and ammonium formate (68 mg, 1.08 mmol) in formamide (5 mL) was heated at 170° C. for 4 hours. After cooling, the mixture was partitioned between ethyl acetate and water. The aqueous layer was extracted with ethyl acetate and the combined organic layers washed with brine, dried over magnesium sulfate, filtered and concentrated. The residue was purified by reverse phase HPLC on a C18 column using 0-70% acetonitrile/0.1% trifluoroacetic acid in water to give 40 mg of the title compound. $^1$H NMR (DMSO-d$_6$) δ 12.57 (br, 1H), 11.14 (s, 1H), 8.15 (s, 1H), 7.53 (s, 1H), 7.30-7.36 (m, 7H), 6.93 (dd, J=8.2, 1.5, 1H), 6.41 (s, 1H).

Example 9

7-(4-hydroxyphenyl)-6-phenylthieno[3,2-d]pyrimidin-4(3H)-one

Example 9A methyl 3-amino-4-(4-hydroxyphenyl)-5-phenylthiophene-2-carboxylate

The title compound was prepared as described in EXAMPLE 8B, using 4-(4,4,5,5-tetramethyl-1,3,2-dioxaborolan-2-yl)phenol in place of 5-(4,4,5,5-tetramethyl-1,3,2-dioxaborolan-2-yl)-1H-indole.

Example 9B 7-(4-Hydroxyphenyl)-6-phenylthieno[3,2-d]pyrimidin-4(3H)-one

The title compound was prepared as described in EXAMPLE 8C using EXAMPLE 9A in place of EXAMPLE 8B. $^1$H NMR (DMSO-d$_6$) δ 12.59 (br, 1H), 9.56 (s, 1H), 8.17 (s, 1H), 7.53 (s, 1H), 7.33-7.38 (m, 5H), 7.10 (d, J=8.5, 2H), 6.74 (d, J=8.5, 2H).

Example 10

2-((dimethylamino)methyl)-6-phenyl-7-m-tolylthieno[3,2-d]pyrimidin-4(3H)-one

Example 10A 7-bromo-2-(chloromethyl)-6-phenylthieno[3,2-d] pyrimidin-4(3H)-one

A mixture of EXAMPLE 8A (1.47 g, 4.7 mmol), chloroacetonitrile (0.43 g, 5.7 mmol) in 4N hydrochloric acid in dioxane (10 mL) was stirred overnight at ambient temperature. The solvent was removed and the residue heated in N,N-dimethylformamide (15 mL) at 110° C. for 2 hours. After cooling, the mixture was partitioned between ethyl acetate and water and the aqueous layer extracted with ethyl acetate. The combined organic layers were washed with brine, dried over magnesium sulfate, filtered, and concentrated. The residue was triturated with 1:1 ethyl acetate/hexanes to give 0.98 g (59%) of the title compound. $^1$H NMR (DMSO-d$_6$) δ 13.13 (s, 1H), 7.75-7.78 (m, 2H), 7.56-7.60 (m, 3H), 4.64 (s, 2H).

Example 10B 7-bromo-2-((dimethylamino)methyl)-6-phenylthieno [3,2-d]pyrimidin-4(3H)-one EXAMPLE 10A (0.19 g, 0.54 mmol) and 2N dimethylamine in methanol (5 mL) were stirred at ambient temperature for 1 hour. The solvent was removed and the residue purified by reverse phase HPLC on a C18 column using 0-70% acetonitrile/0.1% trifluoroacetic acid in water to give 0.18 g (90%) of the title compound. $^1$H NMR (DMSO-$d_6$) δ 13.13 (br, 1H), 7.78-7.79 (m, 2H), 7.57-7.62 (m, 3H), 4.42 (s, 2H), 3.00 (s, 6H).

Example 10C 2-((dimethylamino)methyl)-6-phenyl-7-m-tolylthieno[3,2-d]pyrimidin-4(3H)-one The title compound as the trifluoroacetate salt was prepared as described in EXAMPLE 8B using m-tolylboronic acid in place of 5-(4,4,5,5-tetramethyl-1,3,2-dioxaborolan-2-yl)-1H-indole and EXAMPLE 10B in place of EXAMPLE 8A. $^1$H NMR (DMSO-$d_6$) δ 13.00 (br, 1H), 10.60 (br, 1H), 7.36-7.40 (m, 3H), 7.33-7.35 (m, 2H), 7.22-7.25 (m, 2H), 7.17-7.18 (m, 1H), 7.06 (d, J=7.6 Hz, 1H), 4.40 (s, 2H), 2.95 (s, 6H), 2.28 (s, 3H).

Example 11

(R)-7-bromo-2-((3-hydroxypyrrolidin-1-yl)methyl)-6-phenylthieno[3,2-d]pyrimidin-4(3H)-one To a solution of EXAMPLE 10A (90 mg, 0.25 mmol) in methanol (5 mL) was added (R)-pyrrolidin-3-ol (87 mg, 1 mmol) and the mixture stirred at ambient temperature for 2 days. The solvent was removed and residue purified by flash chromatography on silica gel using 1:10:0.5 methanol/ethyl acetate/concentrated ammonium hydroxide to give the title compound. $^1$H NMR (DMSO-$d_6$) δ 7.75-7.77 (m, 2H), 7.54-7.59 (m, 3H), 4.85 (br, 1H), 4.20 (t, J=6.3 Hz, 1H), 3.69-3.75 (m, 2H), 2.81-2.86 (m, 2H), 2.57-2.58 (m, 2H), 2.01-2.08 (m, 1H), 1.59-1.65 (m, 1H).

Example 12

8-[(3-hydroxyphenylamino)methyl]-5,6,6b,10a-tetrahydro-9H-11-thia-7,9-diaza-benzo[a]fluoren-10-one Example 12A 1-chloro-3,4-dihydronaphthalene-2-carbaldehyde To N,N-dimethylformamide (2.3 mL) at 0° C. was added phosphorus oxychloride (2.33 mL) dropwise and the solution stirred at ambient temperature for 30 minutes. To this solution was added 3,4-dihydronaphthalen-1(2H)-one (1.46 g) and the mixture heated to 45° C. for 1 hour. The mixture was quenched with ice and extracted with diethyl ether. The combined organic layers were washed with water, saturated sodium bicarbonate, and water, dried over magnesium sulfate, filtered, and concentrated to provide 1.9 g of the title compound as a yellow oil, which was used without further purification. $^1$H NMR (DMSO-$d_6$) δ 10.28 (s, 1H), 7.81-7.84 (m, 1H), 7.33-7.50 (m, 3H), 2.82-2.87 (m, 2H), 2.54-2.57 (m, 2H).

Example 12B 1-chloro-3,4-dihydronaphthalene-2-carbaldehyde oxime

A mixture of crude EXAMPLE 12A and hydroxylamine hydrochloride (828 mg) in N,N-dimethylformamide (20 mL) was heated to 110° C. for 8 hours. The mixture was cooled and partitioned between ethyl acetate and water. The organic layer was washed with brine, dried over magnesium sulfate, filtered, and concentrated to provide the title compound as an orange oil, which was used without further purification. $^1$H NMR (DMSO-$d_6$) δ 11.68 (s, 1H), 8.32 (s, 1H), 7.60-7.64 (m, 1H), 7.27-7.33 (m, 3H), 2.81-2.85 (m, 2H), 2.67-2.72 (m, 2H).

Example 12C 1-chloro-3,4-dihydronaphthalene-2-carbonitrile

A solution of crude EXAMPLE 12B in acetic anhydride (20 mL) was heated at reflux for 18 hours. The solution was cooled and partitioned between ethyl acetate and water. The organic layer was washed with brine, dried over magnesium sulfate, filtered, and concentrated to provide 1.70 g (90% over 3 steps) of the title compound. $^1$H NMR (DMSO-$d_6$) δ 7.63-7.66 (m, 1H), 7.32-7.45 (m, 3H), 2.91-2.96 (m, 2H), 2.64-2.69 (m, 2H).

Example 12D methyl 3-amino-2,3,4,5-tetrahydronaphtho[1,2-b]thiophene-2-carboxylate To a solution of EXAMPLE 12C (378 mg) in methanol (3 mL) and tetrahydrofuran (0.5 mL) was added methylthioglycolate (0.18 mL) followed by potassium carbonate (276 mg). The mixture was heated at reflux for 18 hours, filtered through celite and concentrated. The residue was purified by flash chromatography on silica gel using ethyl acetate to provide 459 mg (89%) of the title compound as an orange oil. $^1$H NMR (CDCl$_3$) δ 7.38-7.41 (m, 1H), 7.23 (m, 3H), 5.43 (bs, 2H), 3.85 (s, 3H), 3.00 (t, J=7.8 Hz, 2H), 2.58-2.63 (m, 2H).

Example 12E 8-chloromethyl-5,6,6b,10a-tetrahydro-9H-11-thia-7,9-diaza-benzo[a]fluoren-10-one A solution of EXAMPLE 12D (200 mg) and 2-chloroacetonitrile in 4M hydrochloric acid in dioxane (4 mL) was heated at 65° C. for 18 hours. The mixture was cooled, filtered and the solid heated in N,N-dimethylformamide (6 mL) at 100° C. for 2 hours. The solution was cooled and partitioned between ethyl acetate and water. The organic layer was washed with brine, dried over magnesium sulfate, filtered, and concentrated to provide 145 mg of the title compound as a white solid. $^1$H NMR (DMSO-$d_6$) δ 12.85 (bs, 1H), 7.55 (m, 1H), 7.31-7.38 (m, 3H), 4.60 (s, 2H), 3.01 (t, J=7.3 Hz, 2H), 2.93-2.96 (m, 2H).

Example 12F

8-[(3-hydroxyphenylamino)-methyl]-5,6,6b,10a-tetrahydro-9H-11-thia-7,9-diaza-benzo[a]fluoren-10-one A solution of EXAMPLE 12E (18 mg), diisopropylethylamine and 3-aminophenol (10 mg) in N,N-dimethylformamide (0.5 mL) were heated at 70° C. for 2 hours. The mixture was cooled and purified by HPLC on a C18 column using 0-70% acetonitrile/0.1% trifluoroacetic acid in water to provide 7 mg of the title compound as the trifluoroacetate salt. $^1$H NMR (DMSO-$d_6$) δ 12.29 (s, 1H), 9.01 (s, 1H), 8.17 (bs, 1H), 7.53 (m, 1H), 7.31-7.38 (m, 3H), 6.86 (t, J=7.9 Hz, 1H), 6.11

(m, 1H), 6.06 (t, J=2.1 Hz, 1H), 6.03 (dd, J=7.9, 2.1 Hz, 1H), 4.22 (s, 2H), 3.01 (m, 2H), 2.94-2.96 (m, 2H).

Example 13

9H-7-thia-9,11-diaza-benzo[c]fluoren-8-one

Example 13A 2-chloro-3,4-dihydronaphthalene-1-carbaldehyde

The title compound was prepared as described in EXAMPLE 12A using 3,4-dihydronaphthalen-2(1H)-one in place of 3,4-dihydronaphthalen-1(2H)-one. $^1$H NMR (CDCl$_3$) δ 10.36 (s, 1H), 7.83-7.87 (m, 1H), 7.23-7.26 (m, 3H), 2.90 (m, 4H).

Example 13B 2-chloro-3,4-dihydronaphthalene-1-carbaldehyde oxime

The title compound was prepared as described in EXAMPLE 12B using EXAMPLE 13A in place of EXAMPLE 12A.

Example 13C 2-chloro-3,4-dihydronaphthalene-1-carbonitrile

The title compound was prepared as described in EXAMPLE 12C using EXAMPLE 13B in place of EXAMPLE 12B.

Example 13D methyl 1-amino-4,5-dihydronaphtho[2,1-b]thiophene-2-carboxylate

The title compound was prepared as described in EXAMPLE 12D using EXAMPLE 13C in place of EXAMPLE 12C. $^1$H NMR (DMSO-d$_6$) δ 7.76 (d, J=7.8 Hz, 1H), 7.28-7.33 (m, 2H), 7.20-7.23 (m, 1H), 6.60 (bs, 2H), 3.75 (s, 3H), 2.75-2.89 (m, 4H).

Example 13E 9H-7-thia-9,11-diaza-benzo[c]fluoren-8-one

EXAMPLE 13D (400 mg) and ammonium formate (284 mg) were heated in formamide (10 mL) at 145° C. for 18 hours. The mixture was cooled and partitioned between ethyl acetate and water. The organic layer was washed with brine, dried over magnesium sulfate, filtered, and concentrated. The residue was purified by HPLC on a C18 column using 0-70% acetonitrile/0.1% trifluoroacetic acid in water to provide 15 mg of the title compound. $^1$H NMR (DMSO-d$_6$) δ 12.92 (bs, 1H), 9.86 (d, J=8.1 Hz, 1H), 8.49 (bs, 1H), 8.12-8.21 (m, 3H), 7.76-7.81 (m, 1H), 7.65-7.71 (m, 1H).

Example 14

9-(3-aminopropoxy)-3H-benzo[4,5]thieno[3,2-d]pyrimidin-4-one

Example 14A 2-(3-(1,3-dioxoisoindolin-2-yl)propoxy)-6-fluorobenzonitrile 2-fluoro-6-hydroxybenzonitrile (411 mg, 3 mmol), 2-(3-bromopropyl)isoindoline-1,3-dione (885 mg, 3.3 mmol), and potassium carbonate (1.24 g, 9 mmol) were heated overnight at 70° C. in N,N-dimethylformamide (6 mL). The mixture was cooled, diluted with water, and the precipitate filtered and dried to give 922 mg of the title compound as a white solid. $^1$H NMR (DMSO-d$_6$) δ 7.79-7.87 (m, 4H), 7.69 (td, J=8.6, 6.9 Hz, 1H), 7.01-7.07 (m, 2H), 4.22 (t, J=5.8 Hz, 2H), 3.79 (t, J=6.6 Hz, 2H), 2.11 (quin, J=6.1 Hz, 2H).

Example 14B methyl 3-amino-4-(3-(1,3-dioxoisoindolin-2-yl)propoxy)benzo[b]thiophene-2-carboxylate A mixture of EXAMPLE 14A (0.5 g, 1.54 mmol), methyl thioglycolate (217 μL, 2.31 mmol), and sodium carbonate (653 mg, 6.16 mmol), was heated in methanol (7.7 mL) at 70° C. for 21 hours. The mixture was cooled, diluted with water, and the precipitate filtered and dried. The crude product was purified by flash chromatography on silica gel using a gradient of 0-2% methanol in dichloromethane to provide the title compound as an 85% pure mixture with unreacted EXAMPLE 14A. $^1$H NMR (DMSO-d$_6$) δ 7.79-7.88 (m, 5H), 7.33-7.44 (m, 2H), 6.97 (s, 1H), 6.86 (dd, J=7.8, 1.0 Hz, 1H), 4.23 (t, J=5.8 Hz, 2H), 3.80 (t, J=6.8 Hz, 2H), 3.77 (s, 3H), 2.17 (quin, J=6.1 Hz, 2H).

Example 14C

N-[3-(4-cxo-3,4-dihydrobenzo[4,5]thieno[3,2-d]pyrimidin-9-yloxy)propyl]formamide A mixture of EXAMPLE 14B (194 mg, 0.47 mmol) and ammonium formate (745 mg, 11.8 mmol), was heated in formamide (5 mL) at 150° C. overnight. After cooling, the mixture was diluted with ethyl acetate, and washed with water and brine. The combined aqueous layers were extracted with ethyl acetate. The organic layers were combined, dried over magnesium sulfate, filtered and concentrated. The crude product was purified by flash chromatography on silica gel gel using a gradient of 0-4% methanol in dichloromethane, followed by reverse phase HPLC on a C18 column using a gradient of 0-70% acetonitrile/0.1% TFA in water to provide 19 mg of the title compound as a mixture with 9-hydroxy-3H-benzo[4,5]thieno[3,2-d]pyrimidin-4-one. LCMS m/e 304 (M+H)$^+$.

Example 14D 9-(3-aminopropoxy)-3H-benzo[4,5]thieno[3,2-d]pyrimidin-4-one

A mixture of EXAMPLE 14C (19 mg) and aqueous 1N potassium hydroxide (1 mL) was stirred at ambient temperature for 2 days, neutralized with citric acid solution, concentrated under reduced pressure and slurried with methanol.

The slurry was filtered through a syringe filter rinsing with additional methanol. The filtrate was concentrated and purified by reverse phase HPLC on a C18 column using a gradient of 0-70% acetonitrile/0.1% TFA in water to give 10.5 mg of the title compound as the trifluoroacetate salt. $^1$H NMR (DMSO-$d_6$) δ 13.01 (s, 1H), 8.34 (s, 1H), 8.14 (s, 2H), 7.75 (d, J=7.7 Hz, 1H), 7.63 (t, J=8.1 Hz, 1H), 7.16 (d, J=8.0 Hz, 1H), 4.37 (t, 5.5 Hz, 2H), 3.19-3.26 (m, 2H), 2.16-2.22 (m, 2H).

The foregoing is meant to be illustrative of the invention and not meant to limit it to disclosed embodiments. Variations and changes obvious to one skilled in the art are intended to be within the scope and nature of the invention as defined in the appended claims.

We claim:
1. A compound having formula (I)

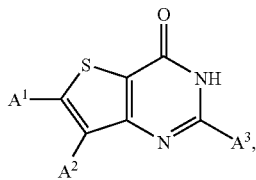

or a salt thereof, wherein
$A^1$ is H or $R^1$;
$A^2$ is H or $R^4$;
$R^1$ is phenyl; which is substituted with one or two of independently selected alkyl, heterocycloalkyl, $OR^{16}$, $SR^{16}$, $S(O)R^{16}$, $SO_2R^{16}$, $C(O)R^{16}$, $CO(O)R^{16}$, $OC(O)R^{16}$, $OC(O)OR^{16}$, $NH_2$, $NHR^{16}$, $N(R^{16})_2$, $C(O)NH_2$, $C(O)NHR^{16}$, $C(O)N(R^{16})_2$, $SO_2NH_2$, $SO_2NHR^{16}$, $SO_2N(R^{16})_2$, $CF_3$, $CF_2CF_3$, $C(O)H$, $C(O)OH$, $OH$, $N_3$, $NO_2$, $OCF_3$, $OCF_2CF_3$, F, Cl, Br or I;
$R^4$ is alkyl, alkenyl or alkynyl, each of which is unsubstituted or substituted with one or two of independently selected $CF_3$, F, Cl, Br or I;
$A^3$ is $R^{15}$;
$R^{15}$ is alkyl, which is substituted with one or two of independently selected $NH_2$, $NHW^1$, $N(W^1)_2$, or heterocycloalkyl; wherein the heterocycloalkyl is unsubstituted or substituted with one or two of independently selected alkyl, $OR^{16}$, or $OH$;
$W^1$ is phenyl or alkyl; wherein the phenyl is unsubstituted or substituted with one or two of independently selected alkyl, $OR^{16}$, $NH_2$, $CF_3$, $CF_2CF_3$, $OH$, $NO_2$, $OCF_3$, $OCF_2CF_3$, F, Cl, Br or I; and
$R^{16}$ is H or alkyl.

2. The compound of claim 1, wherein
$A^2$ is H.

3. A compound having formula (I)

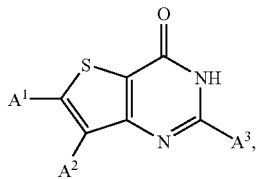

or a salt thereof, wherein
$A^1$ is H or $R^4$;
$A^2$ is H or $R^1$;
$R^1$ is phenyl; which is unsubstituted or substituted with one or two of independently selected alkyl, heterocycloalkyl, $OR^{16}$, $SR^{16}$, $S(O)R^{16}$, $SO_2R^{16}$, $C(O)R^{16}$, $CO(O)R^{16}$, $OC(O)R^{16}$, $OC(O)OR^{16}$, $NH_2$, $NHR^{16}$, $N(R^{16})_2$, $C(O)NH_2$, $C(O)NHR^{16}$, $C(O)N(R^{16})_2$, $SO_2NH_2$, $SO_2NHR^{16}$, $SO_2N(R^{16})_2$, $CF_3$, $CF_2CF_3$, $C(O)H$, $C(O)OH$, $OH$, $N_3$, $NO_2$, $OCF_3$, $OCF_2CF_3$, F, Cl, Br or I;
$R^4$ is alkyl, alkenyl or alkynyl, each of which is unsubstituted or substituted with one or two of independently selected $CF_3$, F, Cl, Br or I;
$A^3$ is $R^{15}$;
$R^{15}$ is alkyl, which is substituted with one or two of independently selected $NH_2$, $NHW^1$, $N(W^1)_2$, or heterocycloalkyl; wherein the heterocycloalkyl is unsubstituted or substituted with one or two of independently selected alkyl, $OR^{16}$, or $OH$;
$W^1$ is phenyl or alkyl; wherein the phenyl is unsubstituted or substituted with one or two of independently selected alkyl, $OR^{16}$, $NH_2$, $CF_3$, $CF_2CF_3$, $NO_2$, $OCF_3$, $OCF_2CF_3$, F, Cl, Br or I; and
$R^{16}$ is H or alkyl.

4. The compound of claim 3, wherein
$A^1$ is H.

5. A compound having formula (I)

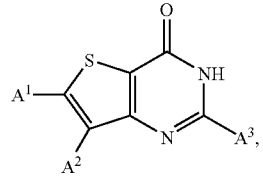

or a salt thereof, wherein
$A^1$ is $R^1$;
$A^2$ is $R^1$;
$R^1$ is phenyl; which is unsubstituted or substituted with one or two of independently selected alkyl, heterocycloalkyl, $OR^{16}$, $SR^{16}$, $S(O)R^{16}$, $SO_2R^{16}$, $C(O)R^{16}$, $CO(O)R^{16}$, $OC(O)R^{16}$, $OC(O)OR^{16}$, $NH_2$, $NHR^{16}$, $N(R^{16})_2$, $C(O)NH_2$, $C(O)NHR^{16}$, $C(O)N(R^{16})_2$, $SO_2NH_2$, $SO_2NHR^{16}$, $SO_2N(R^{16})_2$, $CF_3$, $CF_2CF_3$, $C(O)H$, $C(O)OH$, $OH$, $N_3$, $NO_2$, $OCF_3$, $OCF_2CF_3$, F, Cl, Br or I;
$A^3$ is H or $R^{15}$;
$R^{15}$ is alkyl, alkenyl or alkynyl, each of which is unsubstituted or substituted with one or two of independently selected $NH_2$, $NHW^1$, $N(W^1)_2$, or heterocycloalkyl; wherein the heterocycloalkyl is unsubstituted or substituted with one or two of independently selected alkyl, $OR^{16}$, $SR^{16}$, $S(O)R^{16}$, $SO_2R^{16}$, $C(O)R^{16}$, $CO(O)R^{16}$, $OC(O)R^{16}$, $OC(O)OR^{16}$, $NH_2$, $NHR^{16}$, $N(R^{16})_2$, $C(O)NH_2$, $C(O)NHR^{16}$, $C(O)N(R^{16})_2$, $SO_2NH_2$, $SO_2NHR^{16}$, $SO_2N(R^{16})_2$, $CF_3$, $CF_2CF_3$, $C(O)H$, $C(O)OH$, $OH$, (O), $N_3$, $NO_2$, $OCF_3$, $OCF_2CF_3$, F, Cl, Br or I;
$W^1$ is phenyl or alkyl; wherein the phenyl is unsubstituted or substituted with one or two of independently selected alkyl, $OR^{16}$, $SR^{16}$, $S(O)R^{16}$, $SO_2R^{16}$, $C(O)R^{16}$, $CO(O)R^{16}$, $OC(O)R^{16}$, $OC(O)OR^{16}$, $NH_2$, $NHR^{16}$, $N(R^{16})_2$, $C(O)NH_2$, $C(O)NHR^{16}$, $C(O)N(R^{16})_2$, $SO_2NH_2$, $SO_2NHR^{16}$, $SO_2N(R^{16})_2$, $CF_3$, $CF_2CF_3$, $C(O)H$, $C(O)OH$, $OH$, $N_3$, $NO_2$, $OCF_3$, $OCF_2CF_3$, F, Cl, Br or I; and
$R^{16}$ is H or alkyl.

6. The compound of claim 5, wherein $A^3$ is H.

7. The compound of claim 5, wherein $A^3$ is $R^{15}$, and $R^{15}$ is alkyl, which is unsubstituted.

8. The compound of claim 5, wherein $A^3$ is $R^{15}$, and $R^{15}$ is alkyl, which is substituted with one or two of independently selected $NH_2$, $NHW^1$, $N(W^1)_2$, or heterocycloalkyl; wherein the heterocycloalkyl is unsubstituted or substituted with alkyl, $OR^{16}$ or OH; and $W^1$ is phenyl or alkyl; wherein the phenyl is unsubstituted or substituted with one or two of independently selected alkyl, $OR^{16}$, $NH_2$, $CF_3$, $CF_2CF_3$, OH, $NO_2$, $OCF_3$, $OCF_2CF_3$, F, Cl, Br or I.

* * * * *

UNITED STATES PATENT AND TRADEMARK OFFICE
CERTIFICATE OF CORRECTION

PATENT NO. : 8,148,384 B2
APPLICATION NO. : 11/951546
DATED : April 3, 2012
INVENTOR(S) : Penning et al.

Page 1 of 1

It is certified that error appears in the above-identified patent and that said Letters Patent is hereby corrected as shown below:

In the Claims:

Column 26, line 21, claim 3: "$CF_2CF_3$, $NO_2$" to read as --$CF_2CF_3$, OH, $NO_2$--

Signed and Sealed this
Fifth Day of August, 2014

Michelle K. Lee
*Deputy Director of the United States Patent and Trademark Office*